(12) United States Patent
Kuiper et al.

(10) Patent No.: US 12,398,356 B2
(45) Date of Patent: Aug. 26, 2025

(54) SYSTEMS AND METHODS FOR CENTERING A CIRCULAR OBJECT

(71) Applicant: BD KIESTRA B.V., Drachten (NL)

(72) Inventors: Wouter Kuiper, Marum (NL); Harm W. van der Dong, Den Ham (NL); Jan Bart Van Der Vijver, Groningen (NL); Martijn Kleefstra, Surhuisterveen (NL)

(73) Assignee: BD KIESTRA B.V., Drachten (NL)

( * ) Notice: Subject to any disclaimer, the term of this patent is extended or adjusted under 35 U.S.C. 154(b) by 1137 days.

(21) Appl. No.: 17/259,408

(22) PCT Filed: Jul. 10, 2019

(86) PCT No.: PCT/EP2019/068588
§ 371 (c)(1),
(2) Date: Jan. 11, 2021

(87) PCT Pub. No.: WO2020/011875
PCT Pub. Date: Jan. 16, 2020

(65) Prior Publication Data
US 2021/0269759 A1    Sep. 2, 2021

Related U.S. Application Data

(60) Provisional application No. 62/697,197, filed on Jul. 12, 2018.

(51) Int. Cl.
*B01L 3/00* (2006.01)
*B01L 9/00* (2006.01)
(Continued)

(52) U.S. Cl.
CPC ............... *C12M 23/50* (2013.01); *B01L 9/52* (2013.01); *C12M 23/10* (2013.01);
(Continued)

(58) Field of Classification Search
CPC ........... B01L 2200/02; B01L 2200/025; B01L 2200/18; B01L 2300/021;
(Continued)

(56) References Cited

U.S. PATENT DOCUMENTS 4,222,577 A * 9/1980 Giffin ...................... B28B 1/025
    279/151
5,531,549 A * 7/1996 Fossella ................ B25B 13/467
    279/151
(Continued)

FOREIGN PATENT DOCUMENTS

CN    2602030 Y  *  2/2004
CN    1908154 B  *  8/2010
(Continued)

OTHER PUBLICATIONS

Office action from corresponding Chinese Patent Application No. 2019800462069 dated Feb. 16, 2022, 9 pp.
(Continued)

*Primary Examiner* — Nathan A Bowers
(74) *Attorney, Agent, or Firm* — Botos Churchill IP Law LLP (57) ABSTRACT

The present disclosure describes systems and methods for centering a circular object, such as a petri dish, between a plurality of pins. For example, in one embodiment, a method comprises placing a circular object on a rotatable platform surrounded by three moveable pins. In order to roughly center the circular object, the method further comprises moving, for a first time, all of the pins toward the circular object until at least two out of the three pins are touching the circular object. In order to more accurately center the circular object, the method further comprises: moving all of the pins away from the circular object so that it can be rotated without substantial inference; rotating the platform approximately 60 degrees, wherein rotating the platform
(Continued)

causes the circular object to also rotate by approximately 60 degrees; and moving, for a second time, all of the pins toward the circular object.

13 Claims, 10 Drawing Sheets

(51) Int. Cl.
*C12M 1/00* (2006.01)
*C12M 1/22* (2006.01)

(52) U.S. Cl.
CPC ... *B01L 2200/025* (2013.01); *B01L 2300/021* (2013.01); *B01L 2300/0803* (2013.01)

(58) Field of Classification Search
CPC ..... B01L 2300/0803; B01L 2300/0851; B01L 9/52; B01L 9/56; C12M 23/10; C12M 23/50; G01N 2035/00801
See application file for complete search history.

(56) References Cited

U.S. PATENT DOCUMENTS

| | | | |
|---|---|---|---|
| 6,394,691 B1 * | 5/2002 | Stephan | B23B 31/18 403/374.2 |
| 7,105,338 B1 | 9/2006 | Holmes et al. | |
| 9,446,411 B2 | 9/2016 | Manian et al. | |
| 10,464,794 B2 * | 11/2019 | Figa | F16B 2/185 |
| 2009/0142992 A1 * | 6/2009 | Takahashi | B24B 41/068 451/36 |
| 2014/0050619 A1 * | 2/2014 | Meller | G01N 35/00 422/549 |
| 2014/0377038 A1 | 12/2014 | Malin | |
| 2015/0010996 A1 | 1/2015 | Tsumura et al. | |
| 2015/0276566 A1 | 10/2015 | Berntsen et al. | |
| 2015/0299639 A1 | 10/2015 | Kleefstra et al. | |

FOREIGN PATENT DOCUMENTS

| | | |
|---|---|---|
| CN | 106064121 A | 11/2016 |
| EP | 3228691 A1 | 10/2017 |
| ES | 2759563 T3 * | 5/2020 |
| FR | 2948945 B1 * | 3/2012 |
| JP | 2010515439 A | 5/2010 |
| RU | 114529 U1 | 3/2012 |
| WO | 2008083439 A1 | 7/2008 |
| WO | 2015131662 A1 | 9/2015 |
| WO | 2016191646 A2 | 12/2016 |

OTHER PUBLICATIONS

PCT International Preliminary Report on Patentability and Written Opinion issued in PCT application No. PCT/EP2019/068588 on Jan. 12, 2021.
International Search Report and Written Opinion for International Application No. PCT/EP2019/068588 dated Oct. 11, 2019 (12 pp.).
Office Action issued in corresponding Australian Patent Application No. 2019300262 dated Sep. 20, 2022 (3 pp.).
Office Action issued in corresponding Indian Patent Application No. 202117002374 dated Aug. 25, 2022 (6 pp.).
International Search Report for International Application No. PCT/EP2019/068588 dated Oct. 11, 2019 (4 pages).
Office Action from corresponding Japanese Patent Application No. 2021-500917 dated May 30, 2023 (8 pp.).
Brazilian Office Action issued in BR application No. BR112021000382-7 on Mar. 25, 2025, pp. 17.
Mexican Office Action issued in corresponding MX application No. MX/a/2021/000424 on Jul. 26, 2024, pp. 10.
Decision of Rejection issued in corresponding JP application No. 2021-500917 on Nov. 28, 2024, pp. 8.
Communication from corresponding European Patent Application No. 19749204.4 dated Jul. 13, 2023 (6 pp.).
Office Action from corresponding Brazilian Application No. BR112021000382-7 dated Dec. 19, 2022 (7 pp.).
Office Action from corresponding Russian Application No. 2021102584 dated Nov. 25, 2022 (9 pp.).
Mexican Office Action issued in Mexican Patent Application No. MX/a/2021/000424 on Mar. 5, 2025, pp. 14.

* cited by examiner

SYSTEMS AND METHODS FOR CENTERING A CIRCULAR OBJECT

TECHNICAL FIELD

The present disclosure describes systems and methods for centering a circular object, such as a petri dish, between a plurality of pins.

BACKGROUND

With advancements in computers, networking, and robotics, automation has become a useful tool in streamlining a wide array of workflow processes. For example, automation has been employed in laboratory settings to streamline various processes for preparing biological samples (e.g., patient samples, environmental samples, etc.) for laboratory analysis. Automating such tasks can (a) reduce personnel costs, (b) reduce operator errors (e.g., human errors) that may result, for example, when the operators are tired, distracted, or otherwise unfocused, and (c) reduce the time it takes to analyze samples and report results.

For example, U.S. application Ser. No. 14/674,827 ("the '827 Application"), which was filed on Mar. 31, 2015 and published as U.S. Publication No. 2015/0276566 A1, the disclosure of which is incorporated herein by reference, describes an automated platform for inoculating a variety of receptacles with biological samples for testing and analysis. In some embodiments, the automated platform includes an inoculation module and a streaking module. The inoculation module inoculates receptacles (e.g., petri dishes, plates, broth tubes, slides, etc.), with biological samples. This may be accomplished with a pipette unit, a wire loop, a swab, etc. While inoculating petri dishes, the inoculation module may also dispense a magnetic bead into the petri dishes. After the petri dishes have been inoculated, they may be conveyed along a conveyor system to the streaking module. In some embodiments, the streaking module includes magnets that can cause the magnetic beads deposited in the petri dishes to streak the inoculated media (e.g., blood agar, chocolate agar, MacConkey agar, etc.) with the sample according to a prescribed pattern. After the petri dishes have been streaked, they may be conveyed into an incubation system. Additional details regarding this automated platform may be found in the '827 Application.

As another example, U.S. application Ser. No. 14/687,400 ("the '400 Application"), which was filed on Apr. 15, 2015 and published as U.S. Publication No. 2015/0299639 A1, the disclosure of which is incorporated herein by reference, describes an integrated incubator and image capture module that regulates the incubator atmosphere and obtains high-resolution digital images of sample specimens. In some embodiments, the incubator has a cabinet type enclosure that enables the provision of a controlled environment to the contents of the incubator. In some embodiments, the incubator houses petri dishes that contain nutrient media that has been inoculated by a biological sample. The nutrient media and controlled atmosphere provided to the incubator support the growth of at least certain microbes in the media if present in the sample with which the media has been inoculated. In some embodiments, the image capture module is an enclosed unit immediately adjacent to the incubator. This enables direct transport of petri dishes from the incubator into the image capture module. Once in the image capture module, a lid of a petri dish may be removed such that an image capture unit may electronically image (e.g. digitally photographs) the petri dish. Afterwards, the lid may be replaced and the petri dish may be conveyed back to the incubator. In some embodiments, the images may be automatically analyzed using a software program that can determine if microbial growth has occurred. Additional details regarding this incubator and image capture module may be found in the '400 Application.

As yet another example, International Application No. PCT/US2016/034554 ("the '554 Application"), which was filed on May 27, 2016 and published as International Publication No. WO 2016/191646 A2, the disclosure of which is incorporated herein by reference, describes automated systems for preparing biological samples for both identification (e.g., Matrix Assisted Laser Desorption and Ionization Time-of-Flight Mass Spectrometry ("MALDI-TOF-MS")) and antibiotic susceptibility testing ("AST"). In some embodiments, the automated systems may: locate and select a colony of microorganisms on a culture dish; obtain a sample of the selected colony of microorganisms; prepare a suspension for the obtained sample; dispense a portion of the obtained sample onto a target plate and place the target plate in an apparatus for performing MALDI for identification of the sample of the selected colony of microorganisms; and use or transfer another portion of the suspension for another test, such as AST. The AST could be Kirby-Baur/disk diffusion, disk dilution, broth and agar dilution or other methods. Additional details regarding this automated system may be found in the '554 Application.

In all of the automated systems described above, a petri dish or another similar object may need to be accurately centered. For example, with respect to the '827 Application, a petri dish may need to be accurately centered before it can be inoculated with a biological sample. As another example, with respect to the '400 Application, a petri dish may need to be accurately centered in the image capture module so that the digital images can be accurately compared to detect microbial growth. As yet another example, with respect to the '554 Application, a petri dish may need to be accurately centered before samples can be accurately transferred from the petri dish to a common suspension.

Prior art systems for centering circular objects, such as petri dishes, sometimes include three or more pins. During operation, the pins are moved centrically toward the petri dish until the petri dish is squeezed between all of the pins. However, in such systems, there is a chance that the pins may stop moving when only some (not all) of the pins are touching the petri dish. This may be caused by the friction of the bottom or sides of the petri dish or the pins. In such cases, the petri dish may not be centered properly. As a result, a need exists for systems and methods for robustly and accurately centering circular objects, such as petri dishes.

BRIEF SUMMARY

The present disclosure describes systems and methods for robustly and accurately centering a circular object, such as a petri dish, between a plurality of pins. For example, in one embodiment, a method comprises placing a circular object on a rotatable platform surrounded by three moveable pins. In order to roughly center the circular object, the method further comprises moving, for a first time, all of the pins toward the circular object until at least two out of the three pins are touching the circular object. In order to more accurately center the circular object, the method further comprises: moving all of the pins away from the circular object so that it can be rotated without substantial inference; rotating the platform approximately 60 degrees, wherein rotating the platform causes the circular object to also rotate by approximately 60 degrees; and moving, for a second time, all of the pins toward the circular object.

One aspect of the present disclosure relates to a method comprising: (a) placing a circular object on a platform between three or more pins, wherein the pins are positioned approximately equidistantly from each other, and wherein the pins are in a first open position; (b) moving, for a first time, all of the pins toward the circular object to a closed position, wherein at least two of the pins are in contact with the circular object when the pins are in the closed position; (c) moving all of the pins away from the circular object to the first open position or a second open position, wherein the circular object can be rotated on the platform without interference from the pins when the pins are in the first open position or the second open position; (d) rotating the circular object approximately θ degrees or approximately θ degrees plus one or more complete rotations of 360 degrees, wherein θ is equal to 360 degrees divided by twice the number of pins; and (e) moving, for a second time, all of the pins toward the circular object to the closed position, wherein the circular object is approximately centered between all of the pins after all of the pins have been moved to the closed position for the second time.

In some embodiments, the platform is rotatable and the circular object is rotated by rotating the platform. In some embodiments, the circular object is a petri dish. In some embodiments, the method further comprises inoculating the petri dish with a biological sample after the petri dish has been approximately centered between all of the pins. In some embodiments, the method further comprises capturing an image of the petri dish with an image capture module after the petri dish has been approximately centered between all of the pins. In some embodiments, the method further comprises picking one or more colonies of bacteria in the petri dish after the petri dish has been approximately centered between all of the pins.

Another aspect of the present disclosure relates to a method comprising: (a) placing a circular object on a rotatable platform positioned between three pins, wherein the pins are positioned approximately equidistantly from each other, and wherein the pins are in a first open position; (b) moving, for a first time, all of the pins toward the circular object to a closed position, wherein at least two of the pins are in contact with the circular object when the pins are in the closed position; (c) moving, for a first time, all of the pins away from the circular object to the first open position or a second open position, wherein the circular object can be rotated on the platform without interference from the pins when the pins are in the first open position or the second open position; (d) rotating the platform approximately 60 degrees or approximately 60 degrees plus one or more complete rotations of 360 degrees, wherein rotating the platform causes the circular object to also rotate; and (e) moving, for a second time, all of the pins toward the circular object to the closed position, wherein the circular object is approximately centered between all of the pins after all of the pins have been moved to the closed position for the second time.

In some embodiments, the circular object is a petri dish. In some embodiments, the method further comprises removing a lid covering the petri dish from the petri dish. In some embodiments, the method further comprises inoculating the petri dish with a biological sample after the petri dish has been approximately centered between all of the pins. In some embodiments, the method further comprises: (a) moving, for a second time, all of the pins away from the circular object to the first open position or the second open position after the petri dish has been approximately centered between all of the pins; and (b) orienting the petri dish by rotating the petri dish and aligning a label on the petri dish with a reader positioned near the platform. In some embodiments, the method further comprises capturing an image of the petri dish with an image capture module after the petri dish has been approximately centered between all of the pins and oriented. In some embodiments, the method further comprises picking one or more colonies of bacteria in the petri dish after the petri dish has been approximately centered between all of the pins and oriented.

Yet another aspect of the present disclosure relates to a system comprising: (a) a rotatable platform having a top surface and a bottom surface; (b) a first idler pulley having a top surface and a bottom surface, wherein the top surface of the first idler pulley is fixed to the bottom surface of the platform; (c) a second idler pulley having a top surface and a bottom surface, wherein the second idler pulley is positioned beneath the bottom of the first idler pulley, and wherein three posts are fixed to the bottom of the second idler pulley; and (d) three pins positioned around the rotatable platform, wherein the pins are positioned approximately equidistantly from each other, and wherein each of the pins is fixed to a flap having an arm that extends beneath the second idler pulley, and wherein each of the flaps are connected to a fixed shaft and rotatable about that fixed shaft, and wherein each of the arms of the flaps has a hole surrounding a different one of the posts fixed to the bottom of the second idler pulley, wherein the platform can be rotated by rotating the first idler pulley, and wherein the pins can be moved towards the platform by rotating the second idler pulley.

In some embodiments, the system further comprises: (a) a first motor having a first drive pulley fixed to a shaft of the first motor; (b) a second motor having a second drive pulley fixed to a shaft of the second motor; (c) a first belt connected to the first idler pulley and the first drive pulley; and (d) a second belt connected to the second idler pulley and the second drive pulley, wherein rotational power of the first drive pulley is transferred to first idler pulley through the first belt, and wherein rotational power of the second drive pulley is transferred to second idler pulley through the second belt.

In some embodiments, the system further comprises one or more processors configured to control rotation of the first and second idlers pulleys by controlling the first and second motors. In some embodiments, the one or more processors are configured to: (a) move, for a first time, all of the pins toward a petri dish placed on the platform to a closed position, wherein at least two of the pins are in contact with the petri dish when the pins are in the closed position; (b) move, for a first time, all of the pins away from the petri dish to the first open position or a second open position, wherein the petri dish can be rotated on the platform without interference from the pins when the pins are in the first open position or the second open position; (c) rotate the platform approximately 60 degrees or approximately 60 degrees plus one or more complete rotations of 360 degrees; and (d) move, for a second time, all of the pins toward the petri dish to the closed position, wherein the circular object is approximately centered between all of the pins after all of the pins have been moved to the closed position for the second time.

In some embodiments, the system further comprises a reader and the one or more processors are further configured to: (a) move, for a second time, all of the pins away from the petri dish to the first open position or the second open position after the petri dish has been approximately centered between all of the pins; and (b) orient the petri dish by rotating the platform and aligning a label on the petri dish with the reader. In some embodiments, the system further comprises an image capture module and the one or more processors are further configured to capture an image of the petri dish with the image capture module after the petri dish has been approximately centered between all of the pins and oriented. In some embodiments, the system further comprises an automated pipettor and the one or more processors are further configured to: pick one or more colonies of bacteria in the petri dish after the petri dish has been approximately centered between all of the pins and oriented.

DETAILED DESCRIPTION

Embodiments of the present disclosure are described in detail with reference to the drawing figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1A:
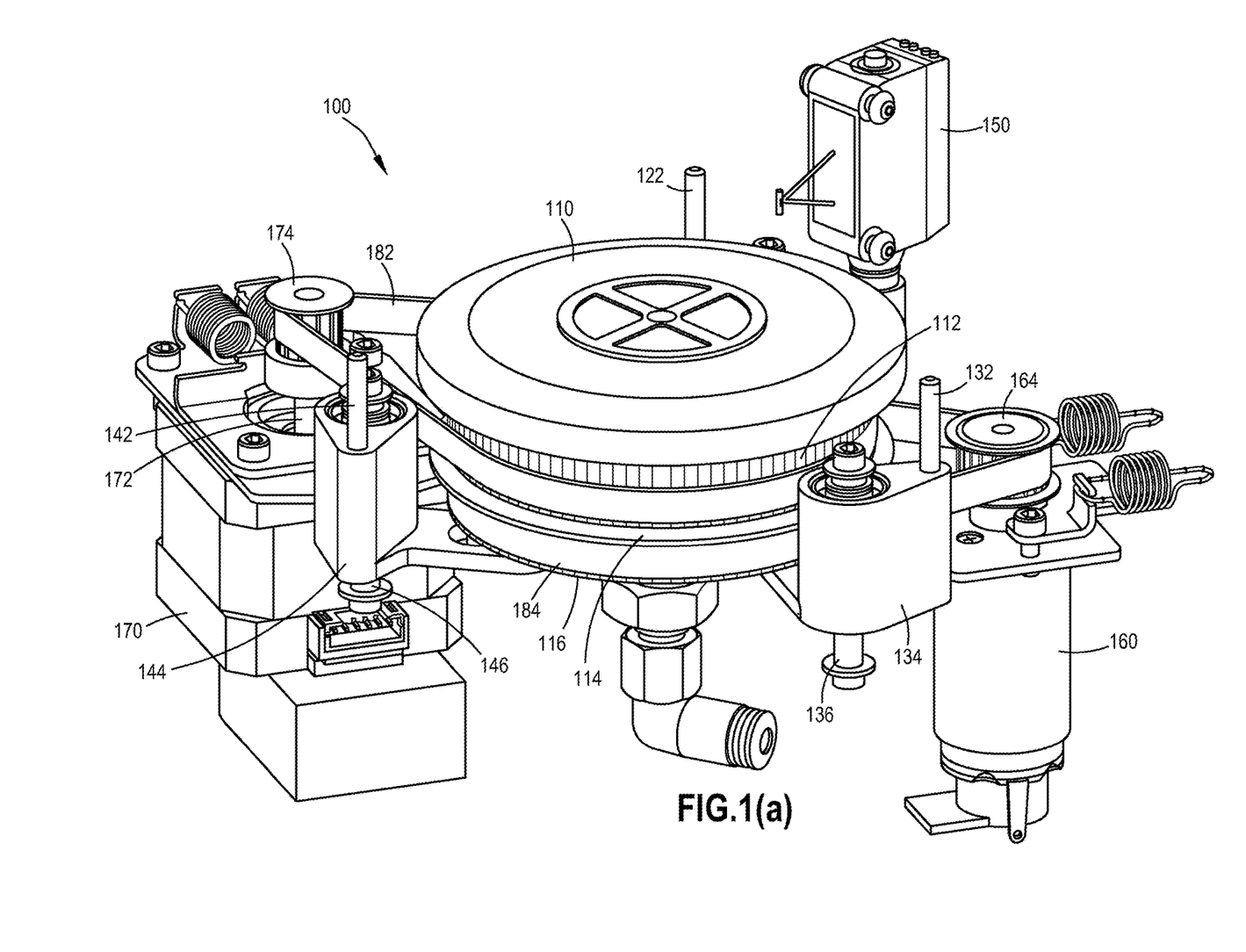
FIG. 1(a) illustrates a side-view of an embodiment of a system for centering a circular object as described herein.
Figure 1B:
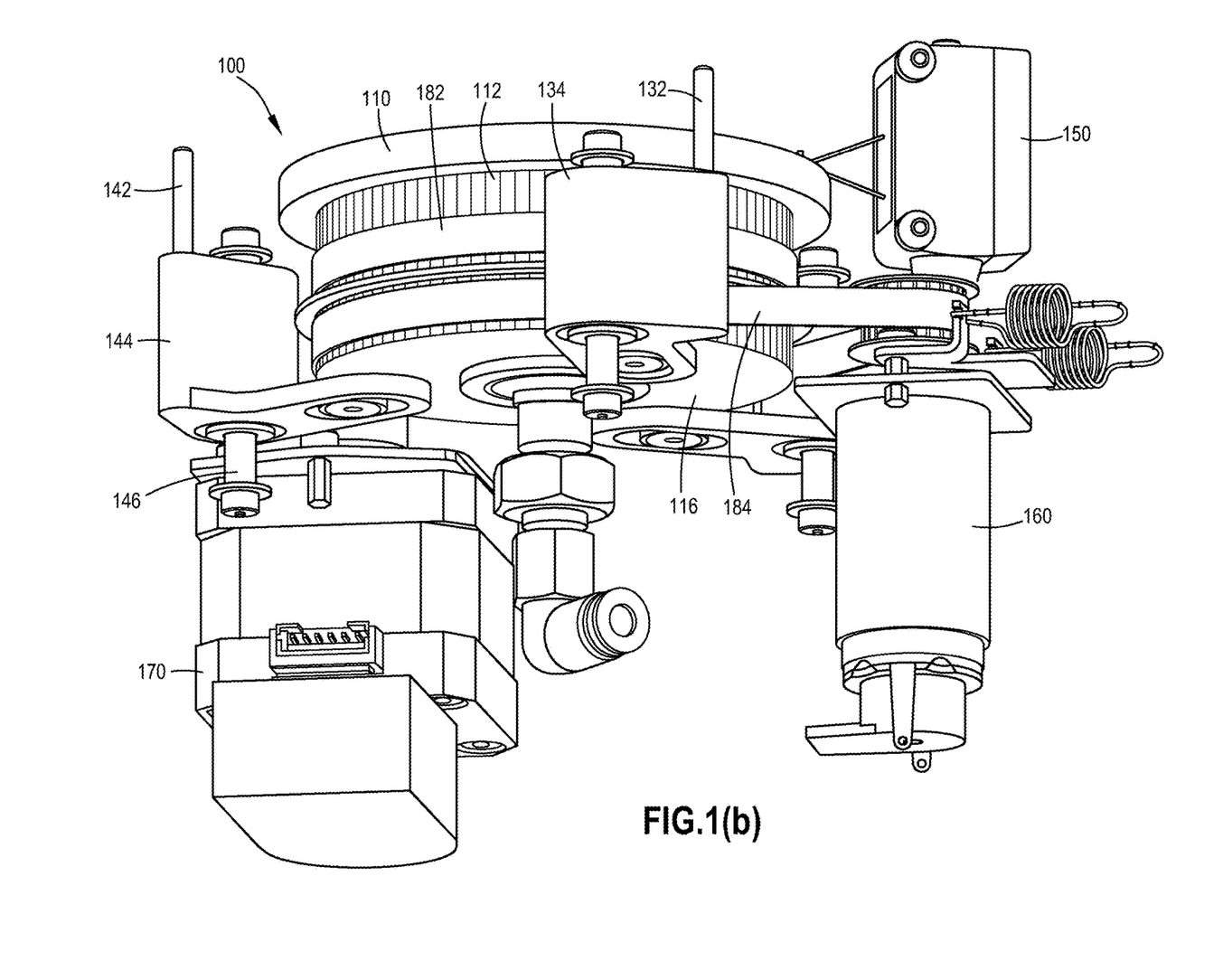
FIG. 1(b) illustrates another side-view of the system of FIG. 1(a).
Figure 1C:
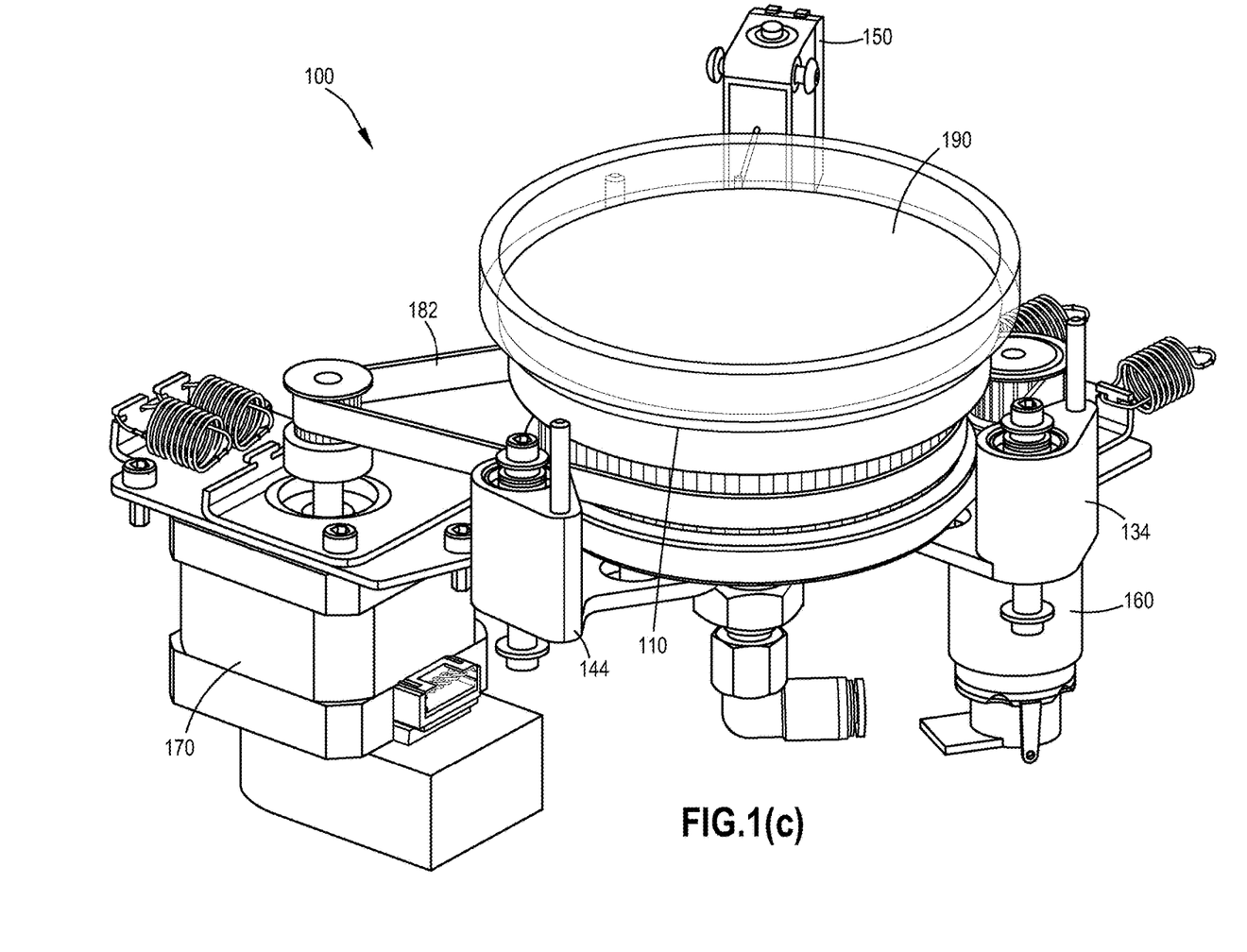
FIG. 1(c) illustrates a side-view of the system of FIG. 1(a) with a petri dish placed on a platform of the system of FIG. 1(a).
Figure 1D:
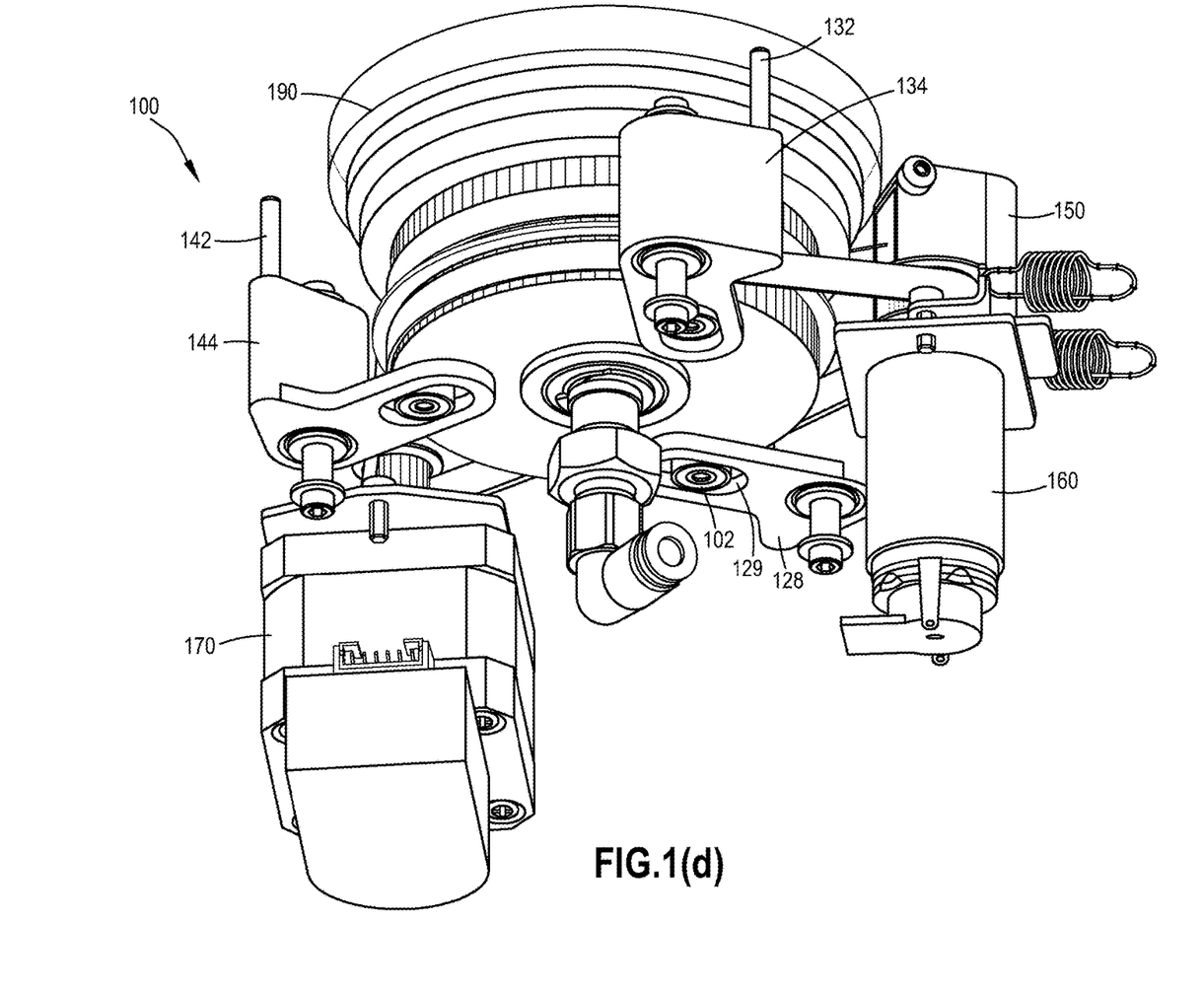
FIG. 1(d) illustrates another side-view of the system of FIG. 1(c).

FIGS. 1(a)-(e) illustrate an embodiment of a system for centering a circular object in accordance with the present technology. As shown, system 100 includes platform 110, pin 122, pin 132, pin 142, sensor 150, motor 160, and motor 170. As shown in FIGS. 1(c) and 1(d), petri dish 190 can be placed on platform 110. In some embodiments, a robotic arm may automatically place petri dish 190 on platform 110. Once on platform 110, pins 122, 132, and 142 may be used to center petri dish 190 on platform 110.

During the centering process, pins 122, 132, and 142 may be moved by motor 160. Motor 160 comprises a shaft (not shown) fixed to drive pulley 164. As used herein, a pulley may be a rotatable structure that is used to transmit power by means of a band, belt, cord, rope, chain, etc. passing over its rim. For example, a pulley may be a smooth wheel-like structure that is configured to transmit power by means of a rubber band or belt. As another example, a pulley may be a gear-like structure that is configured to transmit power by means of a chain. During operation, drive pulley 164 is rotated in a clock-wise or counter-clock-wise direction by the shaft of motor 160. As shown, platform 110 may be positioned above idler pulley 112, divider 114, and idler pulley 116. Divider 114 separates idler pulley 112 and idler pulley 116. While idler pulleys 112 and 116 may be connected through a common shaft (not shown), idler pulleys 112 and 116 rotate independently of one another. During operation, when drive pulley 164 is rotated by motor 160, the rotational power of drive pulley 164 is transferred to idler pulley 116 by belt 184. Belt 184 may be any band, belt, cord, rope, chain, etc. that is capable of transferring the rotational power of drive pulley 164 to idler pulley 116. In other embodiments, idler pulley 116 may be a separate structure positioned, for example, underneath idler pulley 112. In such embodiments, divider 114 may be eliminated.

Figure 1E:
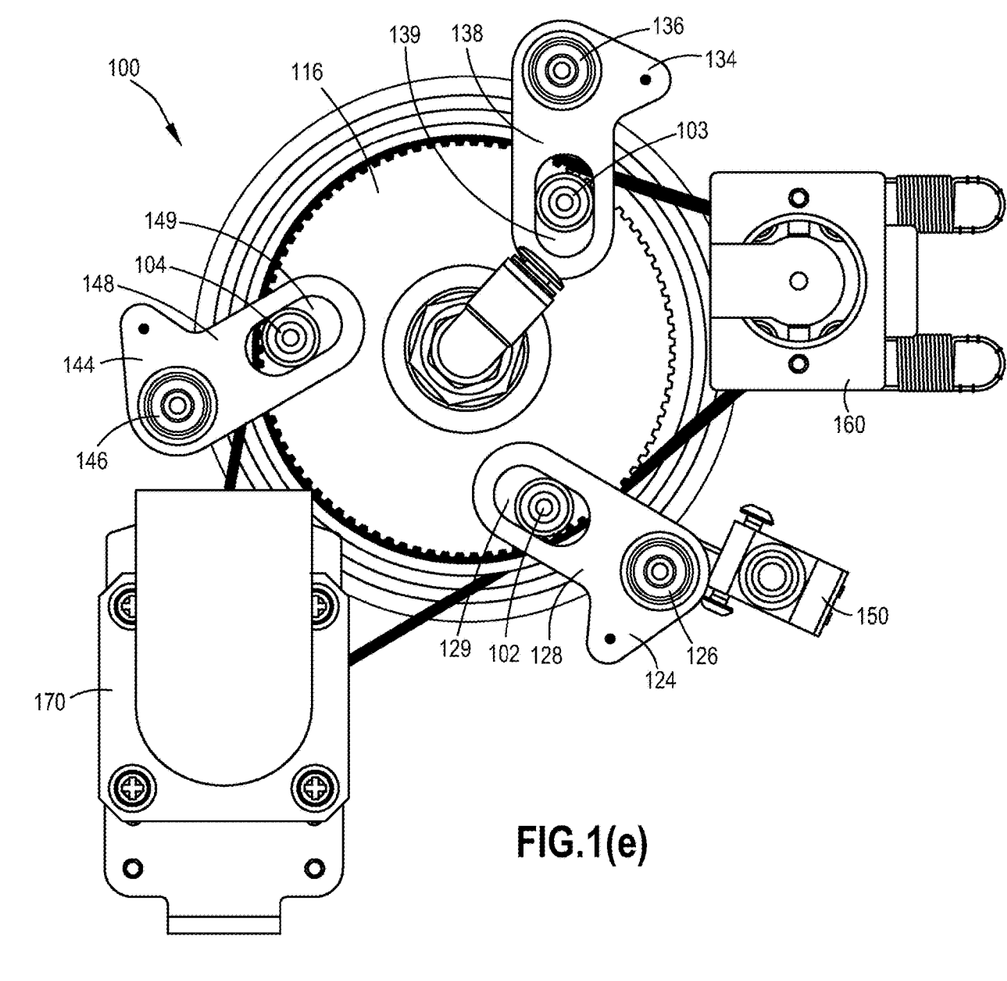
FIG. 1(e) illustrates a bottom-view of the system of FIG. 1(a).

As shown, the rotation of idler pulley 116 in a clock-wise or counter-clock-wise direction causes pins 122, 132, and 142 to move in an inward or outward direction with respect to platform 110. As best shown in FIGS. 1(a)-(d), pins 122, 132, and 142 are fixed to flaps 124, 134, and 144, respectively. Flaps 124, 134, and 144 are connected to and may rotate about shafts 126, 136, and 146, respectively. Shafts 126, 136, and 146 may have fixed positions. For example, shafts 126, 136, and 146 may be fixed to one or more objects (not shown). As best shown in FIG. 1(e), flaps 124, 134, and 144 may comprise arms 128, 138, and 148, respectively. Furthermore, arms 128, 138, and 148 may comprise holes 129, 139, and 149, respectively. Holes 129, 139 and 149 are sized and positioned such that posts 102, 103, and 104, respectively, are positioned inside them. As shown, posts 102, 103, and 104 are fixed to idler pulley 116. As a result, when idler pulley 116 is rotated in a clock-wise or counter-clock-wise direction, posts 102, 103, and 104 also move. In other embodiments, idler pulley 116 and posts 102, 103, and 104 may be formed as a single integrated object. As shown, when pulley 116 is rotated by motor 160, the rotational power of idler pulley 116 is transferred to flaps 124, 134, and 144 through posts 102, 103, and 104, respectively, and arms 128, 138, and 148, respectively. Furthermore, when flaps 124, 134, and 144 move, pins 122, 132, and 142, respectively, may move in an inward or outward direction with respect to platform 110.

During the centering process, platform 110 may be rotated in a clock-wise or counter-clock-wise direction by motor 170. Motor 170 comprises shaft 172 fixed to drive pulley 174. During operation, drive pulley 174 is rotated in a clock-wise or counter-clock-wise direction by shaft 172. As shown, the underside of platform 110 is fixed to the topside of idler pulley 112. In other embodiments, platform 110 and idler pulley 112 may be formed as a single integrated object. Furthermore, as shown, idler pulley 112 is connected to drive pulley 174 by belt 182. During operation, when drive pulley 174 is rotated by motor 170, the rotational power of drive pulley 174 is transferred to idler pulley 112 by belt 182. Moreover, when idler pulley 112 is rotated in a clockwise or counter-clock-wise direction, platform 110 also rotates in the same direction because it is fixed to idler pulley 112. Much like belt 184, belt 182 may also be any band, belt, cord, rope, chain, etc. that is capable of transferring the rotational power of drive pulley 174 to idler pulley 112.

In some embodiments, after petri dish 190 has been centered, petri dish 190 may be inoculated with a biological sample. In some embodiments, one or more of the systems and/or methods disclosed in the '827 Application may be used to inoculate petri dish 190. For example, an automated pipettor may be used to inoculate petri dish 190. In some embodiments, sensor 150 (e.g., an infrared (ID) sensor or an imaging device) may be used to orient petri dish 190. For example, in some embodiments, sensor 150 may be used to determine where a label (e.g., a barcode) on petri dish 190 begins and ends. In some embodiments, after petri dish 190 has been centered and oriented, a reader (not shown) (e.g., a barcode reader or an imaging device) may be used to read (e.g., scan) a label (e.g., a barcode) on petri dish 190. In some embodiments, a reader (not shown) may also be used to further orient petri dish 190. In some embodiments, after petri dish 190 has been centered and oriented, one of more images of petri dish 190 may be captured by an image capture device (not shown) and/or one or more colonies of bacteria may be picked by a robot (not shown). In some embodiments, one or more of the systems and/or methods disclosed in the '400 Application may be used to capture images of petri dish 190. In some embodiments, one or more of the systems and/or methods disclosed in the '554 Application may be used to pick one or more colonies of bacteria in petri dish 190. For example, an automated pipettor may be used to pick one or more colonies of bacteria in petri dish 190.

Figure 2A:
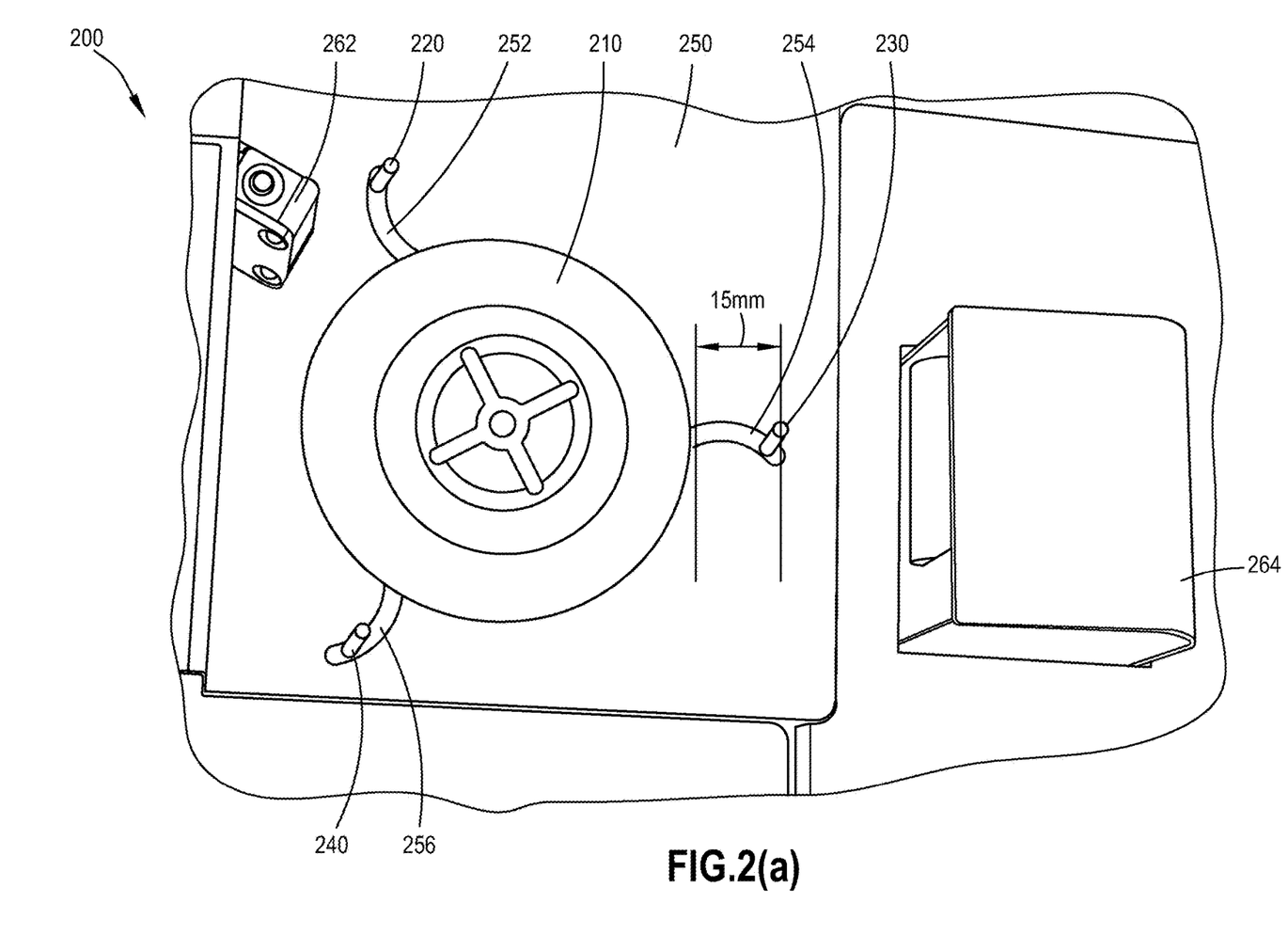
FIG. 2(a) is an image of an embodiment of a system for centering a circular object as described herein.
Figure 2B:
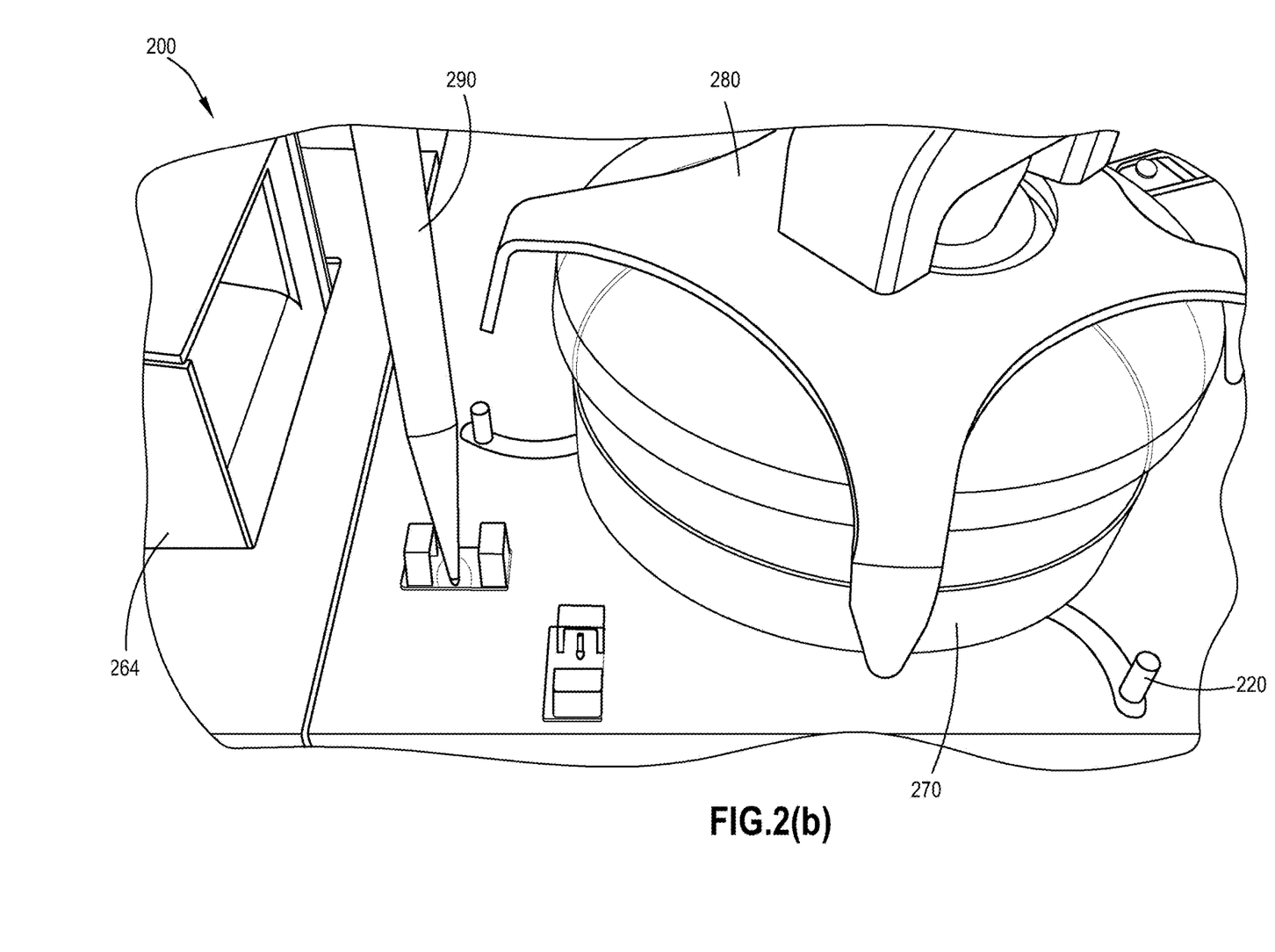
FIG. 2(b) is another image of the system of FIG. 2(a).

FIGS. 2(a)-(b) are photographs of an embodiment of a system for centering a circular object in accordance with the present technology. As shown, system 200 includes platform 210, pin 220, pin 230, pin 240, cover 250, sensor 262, reader 264, robot 280, and automated pipettor 290. Cover 250 includes slits 252, 254, and 256. Underneath cover 250, system 200 may include motors, pulleys, belts, and/or other components much like system 100 of FIGS. 1(a)-(e).

As shown in FIGS. 2(a)-(b), slits 252, 254, and 256 are curved and sized such that the diameters of slits 252, 254, and 256 correspond to the diameters of pins 210, 220, and 230. As a result, pins 220, 230 and 240 can traverse approximately the entire length of the slits 252, 254 and 256. Furthermore, in this embodiment, slits 252, 254, and 256 extend 15 millimeters away from platform 210. However, in other embodiments, the length of slits 252, 254, and 256 can be increased or decreased. For example, the lengths of slits 252, 254 and 256 can be selected to allow a petri dish to be placed onto platform 210 and rotated without substantial interference from pins 220, 230 and 240. As another example, the lengths of slits 252, 254 and 256 may significantly exceed (e.g., by a factor of two or more) the length required to allow a petri dish to be placed onto platform 210 and rotated without substantial interference from the 220, 230 and 240.

During a centering operation, slits 252, 254, and 256 guide pins 210, 220, and 230 as they are advanced toward platform 210. As shown, slits 252, 254, and 256 are curved and have a consistent diameter corresponding to the diameters of pins 210, 220, and 230. In other embodiments, slits 252, 254, and 256 may have different shapes. For example, slits 252, 254, and 256 may be generally straight and have a consistent diameter corresponding to the diameters of pins 210, 220, and 230. As another example, slits 252, 254, and 256 may have conical shapes with variable diameters. In such embodiments, slits 252, 254, and 256 may have narrow portions near platform 210 with diameters corresponding to the diameters of pins 210, 220, and 230.

As shown in FIG. 2(b), petri dish 270 can be placed on platform 210 by robot 280. Once on platform 210, pins 220, 230, and 240 may be used to center petri dish 270 on platform 210. After petri dish 270 has been centered, sensor 262 may also be used to orient petri dish 270. After petri dish 270 has been centered and oriented, reader 264 may be used to read a label on petri dish 270. Reader 264 may also be used to further orient petri dish 270. After petri dish 270 is centered and/or oriented, automated pipettor 290 may be used to inoculate petri dish 270 with a biological sample and/or pick one or more colonies of bacteria in petri dish 270.

Figure 3:
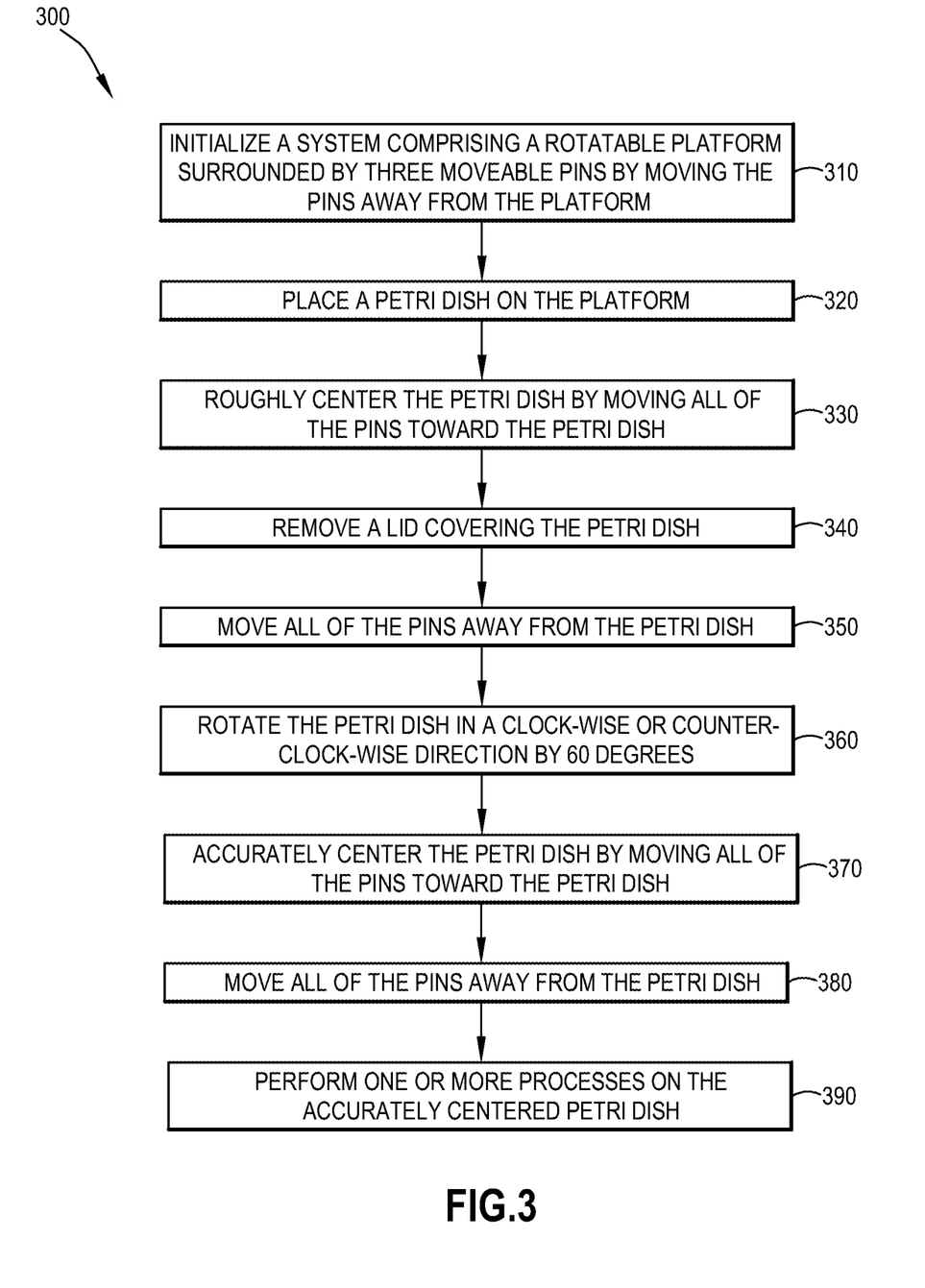
FIG. 3 is a block diagram of a method for centering a circular object as described herein.

FIG. 3 is a block diagram of a method for centering a circular object in accordance with the present technology. Method 300 may be performed with a system, such as system 100 of FIGS. 1(a)-(e) or system 200 of FIGS. 2(a)-(b). In such embodiments, system 100 may include one or more processors configured to control sensor 150, motor 160, and motor 170. Similarly, in such embodiments, system 200 may include one or more processors configured to control sensor 262, reader 264, and/or one or more motors underneath cover 250 that are configured to move platform 210 and pins 220, 230, and 240. It is to be understood that the arrows in FIG. 3 are meant to illustrate one possible order in which the various processes of method 300 may be performed. However, in some embodiments, the blocks illustrated in FIG. 3 may be rearranged. Moreover, in some embodiments, one or more blocks may be added and/or removed.

In block 310, a system comprising a rotatable platform surrounded by three moveable pins is initialized by moving the pins away from the platform to an open position. For example, in an embodiment performed with system 200, pins 220, 230, and 240 may be moved into the open position shown in FIGS. 2(a)-(b). As shown, pins 220, 230, and 240 are moved 15 millimeters away from platform 210. As another example, in an embodiment performed with system 200, pins 220, 230, and 240 may be moved to an open position that is only 8 millimeters away from platform 210. In some embodiments, one or more processors may control the movement of the pins by controlling one or more motors connected to the pins.

In block 320, a petri dish is placed on the platform. For example, in an embodiment performed with system 200, robot 280 may place petri dish 270 on platform 210. As another example, in some embodiments, the petri dish may be conveyed onto the platform through the use of a conveyor system. In some embodiments, one or more processors may control the transfer mechanism (e.g., a robot or a conveyor system) used to place the petri dish on the platform. Since the transfer mechanism may not be configured to accurately center the petri dish on the platform, the petri dish may initially be off-centered.

In block 330, the petri dish is roughly centered by moving all of the pins toward the petri dish into closed positioned. As explained above, some prior art systems use a similar technique to center circular objects, such as petri dishes. However, in contrast to those prior art systems, method 300 includes additional processes for more accurately centering circular objects such as petri dishes, in the systems described herein.

In block 340, a lid covering the petri dish is removed. In other embodiments, this block may be performed at a different place in the illustrated sequence, such as before block 310. In other embodiments, this block may be unnecessary and removed entirely from method 300. For example, in some embodiments, the system may be handling one or more petri dishes that do not have lids or the system may have the capability to obtain an image through a transparent lid, in which case the lid would not need to be removed.

In block 350, all of the pins are moved away from the petri dish to an open position. For example, in an embodiment performed with system 200, pins 220, 230, and 240 may be moved into the position shown in FIGS. 2(a)-(b). As shown, the pins are moved to their original open position, but that is not required. As another example, in some embodiments, the pins may only be moved far enough away so as to allow the petri dish to be rotated without substantial interference. For example, in an embodiment performed with system 200, pins 220, 230, and 240 may be moved to an open position that is only 8 millimeters away from platform 210, instead of an open position that is 15 millimeters away from platform 210 as shown in FIGS. 2(a)-(b).

In block 360, the petri dish is rotated in a clock-wise or counter-clock-wise direction by 60 degrees. For example, in an embodiment performed with system 200, platform 210 may be rotated in a clock-wise or counter-clock-wise direction by 60 degrees in order to rotate petri dish 270 by 60 degrees in the same direction. In some embodiments, one or more processors may control the movement of the platform by controlling one or more motors connected to the pins. Although less time efficient, one skilled in the art will readily appreciate that a similar result can be achieved by adding one or more complete rotations of 360 degrees. For example, the petri dish can be effectively rotated in a clock-wise or counter-clock-wise direction by 60 degrees by rotating the petri dish 420 degrees in a clock-wise or counter-clock-wise direction.

In block 370, the petri dish is accurately centered by moving all of the pins toward the petri dish. As described in more detail below with respect to FIGS. 4(a)-(l), during block 330, at least two of the three pins should contact the petri dish. Therefore, the edge of the petri dish that is farthest from the center of platform is located between the two contacting pins. As a result, by rotating the petri dish, one of the pins that contacted the petri dish during block 330 can be used during block 370 to more accurately urge the petri dish into the center of the platform.

In block 380, all of the pins are moved away from the petri dish. This block is optional. In some embodiments, it may be advantageous to move the pins away from the petri dish before one or more additional processes are performed on the petri dish. For example, if the petri dish needs to be rotated again in order to be oriented properly, it may be advantageous to move the pins away from the petri dish before rotating it. In other embodiments, it may be more advantageous to keep the pins in a position that is close the petri dish and the platform in order to prevent the petri dish from moving and becoming off-center.

In block 390, one or more processes are performed on the accurately centered petri dish. For example, in block 390, the petri dish may be inoculated with a biological sample. In some embodiments, one or more of the systems and/or methods disclosed in the '827 Application may be used to inoculate the petri dish. As another example, in block 390, one of more images of the petri dish may be captured by an image capture device. In some embodiments, one or more of the systems and/or methods disclosed in the '400 Application may be used to capture the images of the petri dish. As yet another example, in block 390, one or more colonies of bacteria in the petri dish may be picked by a robot. In some embodiments, one or more of the systems and/or methods disclosed in the '554 Application may be used to pick one or more colonies of bacteria in petri dish 190.

Figure 4A:
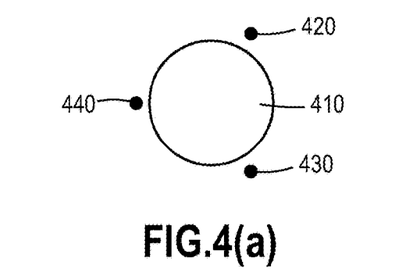
FIGS. 4(a)-(l) illustrate a method for centering a circular object as described herein.

FIGS. 4(a)-(l) illustrate a method for centering a circular object in accordance with the present technology. More specifically, with reference to method 300 of FIG. 3, the processes illustrated in FIGS. 4(a)-(d) correspond to block 330, the processes illustrated in FIG. 4(e) correspond to block 350, the processes illustrated in FIGS. 4(f)-(g) correspond to block 360, the processes illustrated in FIGS. 4(h)-(j) correspond to block 370, and the processes illustrated in FIGS. 4(k)-(l) correspond to block 380. As shown, FIGS. 4(a)-(l) illustrate petri dish 410 positioned between moveable pins 420, 430, and 440. As shown in FIG. 4(a), pins 420, 430, and 440 are in an open position.

Figure 4B:
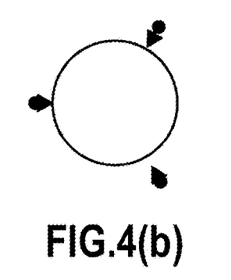
Figure 4C:
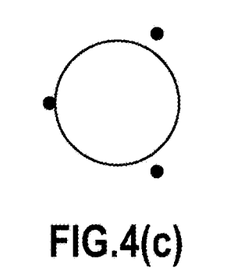
Figure 4D:
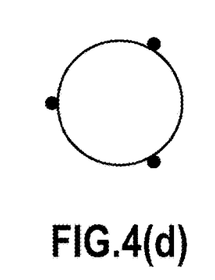

In FIGS. 4(b)-(d), pins 420, 430, and 440 are moved toward petri dish 410 to a closed position. As shown in FIG. 4(c), during this process, pin 440 contacts petri dish 410 before the other pins. Furthermore, as shown in FIG. 4(d), pin 420 eventually contacts petri dish 410, but pin 430 does not make contact with petri dish 410 because it has reached the limit of its travel trajectory through its respective slit (not shown) before making contact with petri dish 410. As a result, petri dish 410 is not accurately centered in FIG. 4(d). More specifically, the edge of petri dish that is farthest from the center of pins 420, 430, and 440 is located between pins 440 and 420. Furthermore, the edge of petri dish that is closest to the center of pins 420, 430, and 440 is located by pin 430.

Figure 4E:
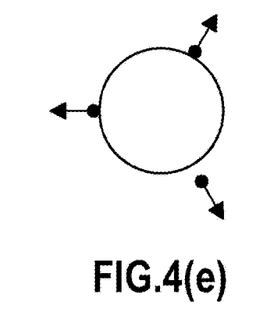
Figure 4F:
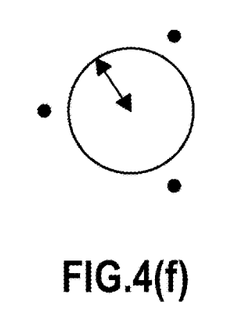
Figure 4G:
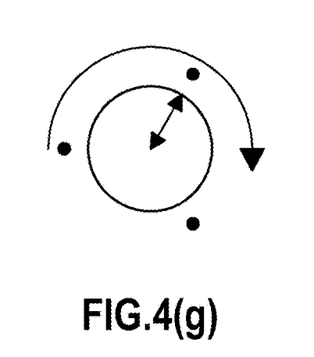
Figure 4H:
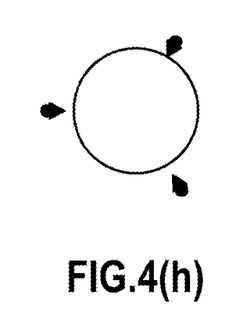
Figure 4I:
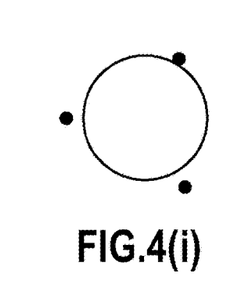
Figure 4J:
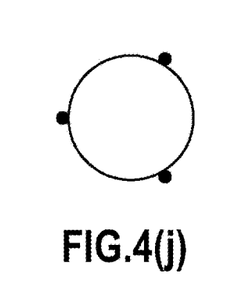
Figure 4K:
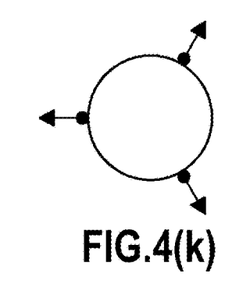
Figure 4L:
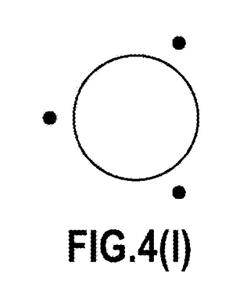

In order to more accurately center petri dish 410, in FIG. 4(e), pins 420, 430, and 440 are moved away from petri dish 410 to an open position. Subsequently, in FIGS. 4(f)-(g), petri dish 410 is rotated 60 degrees in a clock-wise direction. As a result, the edge of petri dish that is farthest from the center of pins 420, 430, and 440 is now located by pin 420. In FIGS. 4(h)-(j), pins 420, 430, and 440 are again moved toward petri dish 410 to a closed position. As shown in FIG. 4(i), during this process, pin 420 contacts petri dish 410 before the other pins. As a result, pin 420 is able to push petri dish 410 into a position that is more accurately centered between all of the pins. Lastly, in FIGS. 4(k)-(l), pins 420, 430, and 440 are again moved away from petri dish 410 to an open position.

Figure 5:
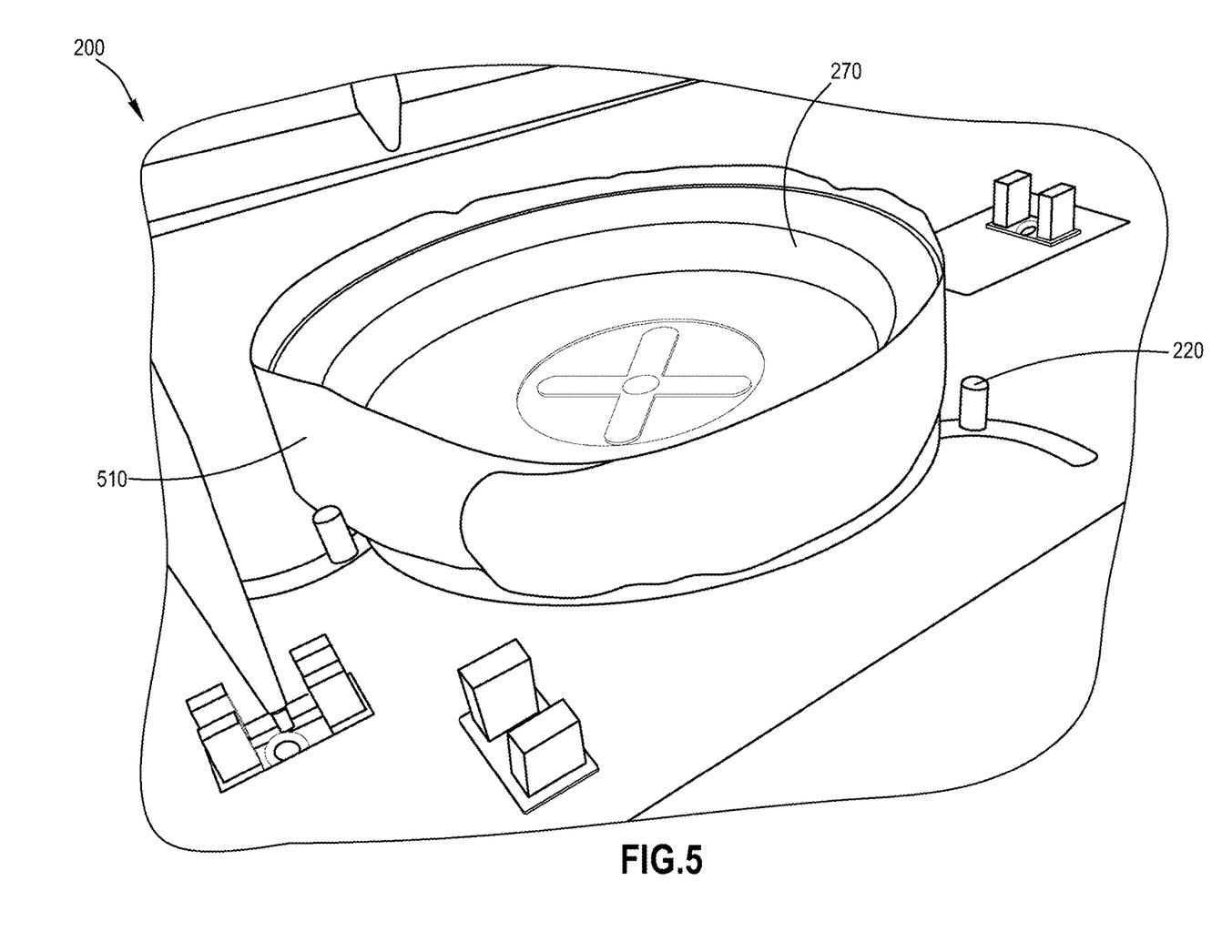
FIG. 5 is an image of a test performed to demonstrate the operation of the system of FIGS. 2(a)-(b).

FIG. 5 is a photograph of a simple experiment performed with the system of FIGS. 2(a)-(b) in order to demonstrate some of the advantages of the present technology. As shown, a piece of double-sided tape 510 was wrapped around petri dish 270. Furthermore, at the time the image was taken, petri dish 270 had only been placed on platform 210 (see, e.g., block 320 of FIG. 3) and pins 220, 230, and 240 had only been moved toward petri dish once (see, e.g., block 330 of FIG. 3). As can be seen, at this point in time, there is a significant gap between pin 220 and petri dish 270, which indicates that petri dish 270 is not accurately centered.

As mentioned above, some prior art systems for centering a petri dish include three or more pins. During operation, the pins are moved toward the petri dish until the petri dish is squeezed between all of the pins. However, without more, these types of prior art systems may fail to accurately center the petri dish because of the friction of the bottom or sides of the petri dish or the pins. Although petri dishes often have smooth low-friction surfaces, various situations may arise that change this. For example, some of the agar in the petri dish may spill and make the sides of the petri dish sticky. As another example, a label printed onto a petri dish may begin to peel and some of the adhesive on the back of that label may become exposed. As yet another example, a label may be printed unevenly onto a petri dish. As a result, as shown in FIG. 5, there is chance that the pins may stop moving when only some (not all) of the pins are touching the petri dish. Embodiments of the present technology mitigate these risks.

Moreover, some of the advantages of the present technology over the prior art can be realized despite certain inaccuracies. For example, in block 360 of FIG. 3, the petri dish is rotated by 60 degrees in a clock-wise or counter-clock-wise direction. However, with respect to the position of the petri dish after performing block 330, the petri dish can be more accurately centered even if it is only rotated, for example, by 55 degrees in a clock-wise or counter-clock-wise direction. Similarly, with respect to the position of the petri dish after performing block 330, the petri dish can be more accurately centered even if it is rotated, for example, by 65 degrees in a clock-wise or counter-clock-wise direction. Therefore, as used herein, "approximately 60 degrees" is equivalent to saying "60 degrees plus or minus five degrees." Thus, "approximately 60 degrees" is equivalent to, for example, 55 degrees, 56.7 degrees, 57.1 degrees, 59.021 degrees, 61.78 degrees, 62.35 degrees, and 64.99 degrees.

From the foregoing and with reference to the various figure drawings, those skilled in the art will appreciate that certain modifications can also be made to the present disclosure without departing from the scope of the same. For example, different mechanisms can be used to rotate a circular object. For example, in some embodiments, a circular object, such as a petri dish, may be placed on a stationary platform between a plurality of pins. In such embodiments, a robot positioned above the circular object may grab the petri dish and rotate it.

As another example, the present technology can be readily adapted to systems with four or more pins. For example, a system may comprise a rotatable platform surrounded by four moveable pins. Such a system could be used in method 300 of FIG. 3 if, in block 360, the petri dish is only rotated approximately 45 degrees in a clock-wise or counter-clock-wise direction. In fact, the amount of rotation performed in block 360 can be stated more generally as:

$$\theta = \frac{360°}{2P},$$

where θ is the amount by which the petri dish is rotated and P is the number of pins surrounding the petri dish. Furthermore, one skilled in the art will readily appreciate that one or more complete rotations of 360 degrees can be added to θ. As with the previous embodiment, "approximately 45 degrees" is equivalent to saying "45 degrees plus or minus five degrees."

Furthermore, while several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A method comprising:
placing a circular object on a platform between three or more pins, wherein the pins are positioned approximately equidistantly from each other, and wherein the pins are in a first open position;
moving, for a first time, all of the pins toward the circular object to a closed position, wherein at least two of the pins are in contact with the circular object when the pins are in the closed position;
moving all of the pins away from the circular object to the first open position or a second open position, wherein the circular object can be rotated on the platform without interference from the pins when the pins are in the first open position or the second open position;
rotating the circular object approximately θ degrees or approximately θ degrees plus one or more complete rotations of 360 degrees, wherein θ is equal to 360 degrees divided by twice a number of pins; and
moving, for a second time, all of the pins toward the circular object to the closed position, wherein the circular object is approximately centered between all of the pins after all of the pins have been moved to the closed position for the second time.

2. The method of claim 1, wherein the platform is rotatable, and wherein the circular object is rotated by rotating the platform.

3. The method of claim 1, wherein the circular object is a petri dish.

4. The method of claim 3, further comprising:
inoculating the petri dish with a biological sample after the petri dish has been approximately centered between all of the pins.

5. The method of claim 3, further comprising:
capturing an image of the petri dish with an image capture module after the petri dish has been approximately centered between all of the pins.

6. The method of claim 3, further comprising:
picking one or more colonies of bacteria in the petri dish with an automated pipettor after the petri dish has been approximately centered between all of the pins.

7. A method comprising:
placing a circular object on a rotatable platform positioned between three pins, wherein the pins are positioned approximately equidistantly from each other, and wherein the pins are in a first open position;
moving, for a first time, all of the pins toward the circular object to a closed position, wherein at least two of the pins are in contact with the circular object when the pins are in the closed position;
moving, for a first time, all of the pins away from the circular object to the first open position or a second open position, wherein the circular object can be rotated on the platform without interference from the pins when the pins are in the first open position or the second open position;
rotating the platform approximately 60 degrees or approximately 60 degrees plus one or more complete rotations of 360 degrees, wherein rotating the platform causes the circular object to also rotate; and
moving, for a second time, all of the pins toward the circular object to the closed position, wherein the circular object is approximately centered between all of the pins after all of the pins have been moved to the closed position for the second time.

8. The method of claim 7, wherein the circular object is a petri dish.

9. The method of claim 8 further comprising:
removing a lid covering the petri dish from the petri dish.

10. The method of claim 9 further comprising:
inoculating the petri dish with a biological sample after the petri dish has been approximately centered between all of the pins.

11. The method of claim 9 further comprising:
moving, for a second time, all of the pins away from the circular object to the first open position or the second open position after the petri dish has been approximately centered between all of the pins; and orienting the petri dish by rotating the petri dish and aligning a label on the petri dish with a reader positioned near the platform.

12. The method of claim 11 further comprising:

capturing an image of the petri dish with an image capture module after the petri dish has been approximately centered between all of the pins and oriented.

13. The method of claim 11 further comprising:

picking one or more colonies of bacteria in the petri dish after the petri dish has been approximately centered between all of the pins and oriented.

* * * * *